(12) United States Patent
Hauswald

(10) Patent No.: US 10,086,132 B2
(45) Date of Patent: Oct. 2, 2018

(54) INFUSION DEVICE

(71) Applicant: STC.UNM, Albuquerque, NM (US)

(72) Inventor: Mark Hauswald, Telluride, CO (US)

(73) Assignee: STC.UNM, Albuquerque, NM (US)

( * ) Notice: Subject to any disclaimer, the term of this patent is extended or adjusted under 35 U.S.C. 154(b) by 153 days.

(21) Appl. No.: 15/330,023

(22) Filed: Jul. 26, 2016

(65) Prior Publication Data
US 2016/0339169 A1 Nov. 24, 2016

Related U.S. Application Data

(63) Continuation-in-part of application No. 14/544,032, filed on Nov. 17, 2014, now Pat. No. 9,744,292, which is a continuation-in-part of application No. 13/815,405, filed on Feb. 28, 2013, now Pat. No. 8,920,382.

(60) Provisional application No. 61/607,832, filed on Mar. 7, 2012.

(51) Int. Cl.
A61M 5/315 (2006.01)
A61M 5/145 (2006.01)
A61M 5/14 (2006.01)
A61M 5/142 (2006.01)
A61M 5/168 (2006.01)

(52) U.S. Cl.
CPC ........ A61M 5/1452 (2013.01); A61M 5/1413 (2013.01); A61M 5/1454 (2013.01); A61M 5/14216 (2013.01); A61M 5/1422 (2013.01); A61M 5/16809 (2013.01); A61M 5/31535 (2013.01); A61M 2202/048 (2013.01)

(58) Field of Classification Search
CPC .. A61M 2005/1405; A61M 2005/3115; A61M 5/1424; A61M 5/3158; A61M 5/31565
See application file for complete search history.

(56) References Cited

U.S. PATENT DOCUMENTS

| | | | |
|---|---|---|---|
| 6,270,481 B1 | 8/2001 | Mason et al. | 604/181 |
| 6,719,728 B2 | 4/2004 | Mason et al. | 604/181 |
| 7,458,956 B1 | 12/2008 | Adams et al. | 604/158 |
| 8,016,790 B2 | 9/2011 | Walborn et al. | 604/153 |
| 8,308,457 B2 | 11/2012 | Goldor | 417/479 |
| 8,920,382 B1 | 12/2014 | Hauswald | 604/183 |
| 8,961,462 B2 | 2/2015 | Morten et al. | 604/135 |
| 2007/0299408 A1 | 12/2007 | Alferness et al. | 604/250 |
| 2011/0184348 A1 | 7/2011 | Bates | 604/131 |
| 2015/0141957 A1 | 5/2015 | Hauswald | 604/507 |

Primary Examiner — Deanna K Hall

(57) ABSTRACT

A mechanical infusion pump device for injecting medication into a patient's IV, includes an IV reservoir and a syringe communicated to the IV reservoir and having a syringe plunger connected to a filling plunger that is moved with the syringe plunger in a first syringe-filling direction to fill the syringe with fluid medication. Biasing weight(s) is/are provided on the filling plunger for exerting bias or force from gravity on the filling plunger and the syringe plunger in a second syringe-discharging direction to dispense medication from the syringe into the patient's IV when the filling plunger is released. Only a calibrated amount of medicine can be discharged to the patent's IV over time as determined by calibration of the biasing weights and the metering element located between the syringe and the patient's IV for a given viscosity of the medication.

10 Claims, 5 Drawing Sheets

INFUSION DEVICE

RELATED APPLICATION

This application is a continuation-in-part of U.S. application Ser. No. 14/544,032 filed Nov. 17, 2014, which is a continuation-in-part of U.S. application Ser. No. 13/815,405 filed Feb. 28, 2013, which claims benefits and priority of U.S. provisional application Ser. No. 61/607,832 filed Mar. 7, 2012, the entire disclosures of all of which are incorporated herein by reference.

FIELD OF THE INVENTION

This invention relates generally to an infusion pump device and, more specifically, to a mechanical, low cost, and disposable infusion pump device that meters a controlled amount of medication per unit of time to a patient.

BACKGROUND OF THE INVENTION

A problem for critical care medical treatment in the developing world and during transport of patients is that available infusion pumps are expensive, fragile, and require electricity to operate. The alternative to an infusion pump is for the caregiver to watch and count drips in an IV chamber. However, this technique is inaccurate and hence risky. For obstetricians and midwives, oxytocin infusions during difficult birthing (labor) present problems in particular, because the only alternative may be performance of a C-section.

SUMMARY OF THE INVENTION

To this end, the present invention provides in one embodiment an infusion device, especially for use for birthing, critical care or emergency patients, although the invention is not limited to any particular patient use. In an illustrative embodiment of the present invention, infusion pump device comprises an IV medication reservoir, a syringe communicated to the IV medication reservoir and having a syringe plunger movable in a first syringe-filling direction, a filling plunger operable by an individual to engage and move the syringe plunger in the first direction against a biasing element wherein the biasing element exerts bias on the syringe plunger when the syringe is filled to move it in a second syringe-discharging direction to dispense an amount of medication per unit of time to a patient's IV. The filling plunger is movable independently of the syringe plunger and is engaged with but unconnected to the syringe plunger when the filling plunger is moved in the first direction to fill the syringe. Release of the filling plunger permits the biasing element to move the syringe plunger in the second direction to dispense medication.

In a particular embodiment of the present invention, the syringe is communicated to the patient's IV by a fixed or adjustable metering element that, together with the biasing element, is/are calibrated to allow discharge of a calibrated amount of medication per unit of time. One-way valves are provided between the IV medication reservoir and the syringe and between syringe and the patient's IV to permit the drawing of medication from the IV reservoir into the syringe and dispensing of the medication to the patient's IV.

The present invention also envisions a method of injecting medication into a patient's IV comprising the steps of drawing medication from an IV medication reservoir into a syringe by manually moving the filling plunger to engage and move the syringe plunger in a first syringe-filling direction to fill the syringe and then using the biasing element to exert bias on the plunger of the syringe in a second, syringe-discharging direction to dispense a calibrated amount of medication over time into the patient's IV when the filling plunger is released In an alternate embodiment of the invention when only small quantities of medication are needed, the syringe can be preloaded with the desired quantity that is discharged into the patient's IV bag using the biasing element without the need for use of the filling plunger, IV medication reservoir, and the one-way valve associated with the IV medication reservoir and then the medication is dispensed into the patient's IV bag using the bias of the biasing element.

In another different embodiment, the present invention provides an infusion pump device comprising an IV medication reservoir, a syringe communicated to the IV medication reservoir and having a syringe plunger operable by an individual to move the syringe plunger in a first syringe-filling direction. The syringe plunger includes a biasing weight-receiving feature (e.g. a platform) thereon on which one or more biasing weights are received to exert a bias or force by gravity on the syringe plunger in a second syringe-discharging direction when the syringe is filled and the syringe plunger is released to move the syringe plunger in the second syringe-discharging direction to dispense an amount of medication per unit of time to a patient's IV. Release of the syringe plunger permits the one or more biasing weights to move the syringe plunger in the second direction to dispense medication.

In still another different embodiment, the present invention provides an infusion pump device comprising an IV medication reservoir, a syringe communicated to the IV medication reservoir and having a syringe plunger movable in a first syringe-filling direction, and a filling plunger connected to the syringe plunger so as to move as a unit and operable by an individual to move the syringe plunger in the first direction. The filling plunger includes a biasing weight-receiving feature (e.g. surface, platform, hooks.) on which one or more biasing weights are received to exert a bias or force by gravity on the syringe plunger in a second syringe-discharging direction when the syringe is filled and the filling plunger is released to move the syringe plunger in the second syringe-discharging direction to dispense an amount of medication per unit of time to a patient's IV. Release of the filling plunger permits the one or more biasing weights to move the syringe plunger in the second direction to dispense medication.

The infusion pump device and method pursuant to the present invention are advantageous especially for use for the birthing or critical care patient. The device and method provide quick and easy set-up and use.

These and other advantages will become more apparent from the following detailed description taken with the following drawings.

DETAILED DESCRIPTION OF THE INVENTION

Figure 1A:
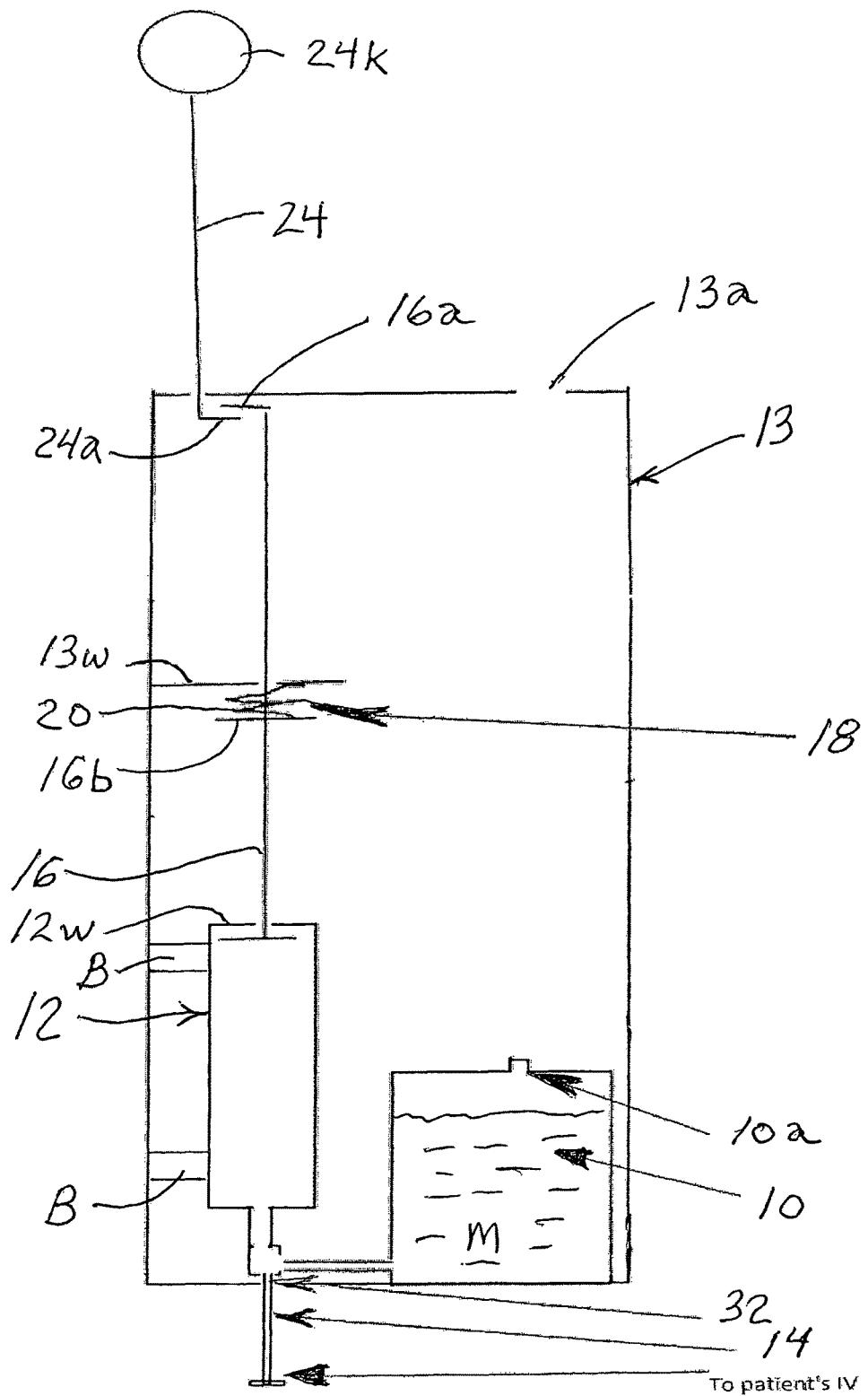
FIGS. 1A and 1B schematically show an illustrative embodiment of a mechanical infusion pump device according to an illustrative embodiment of the present invention wherein FIG. 1A the biasing element is shown compressed and in FIG. 1B is shown extended.
Figure 1B:
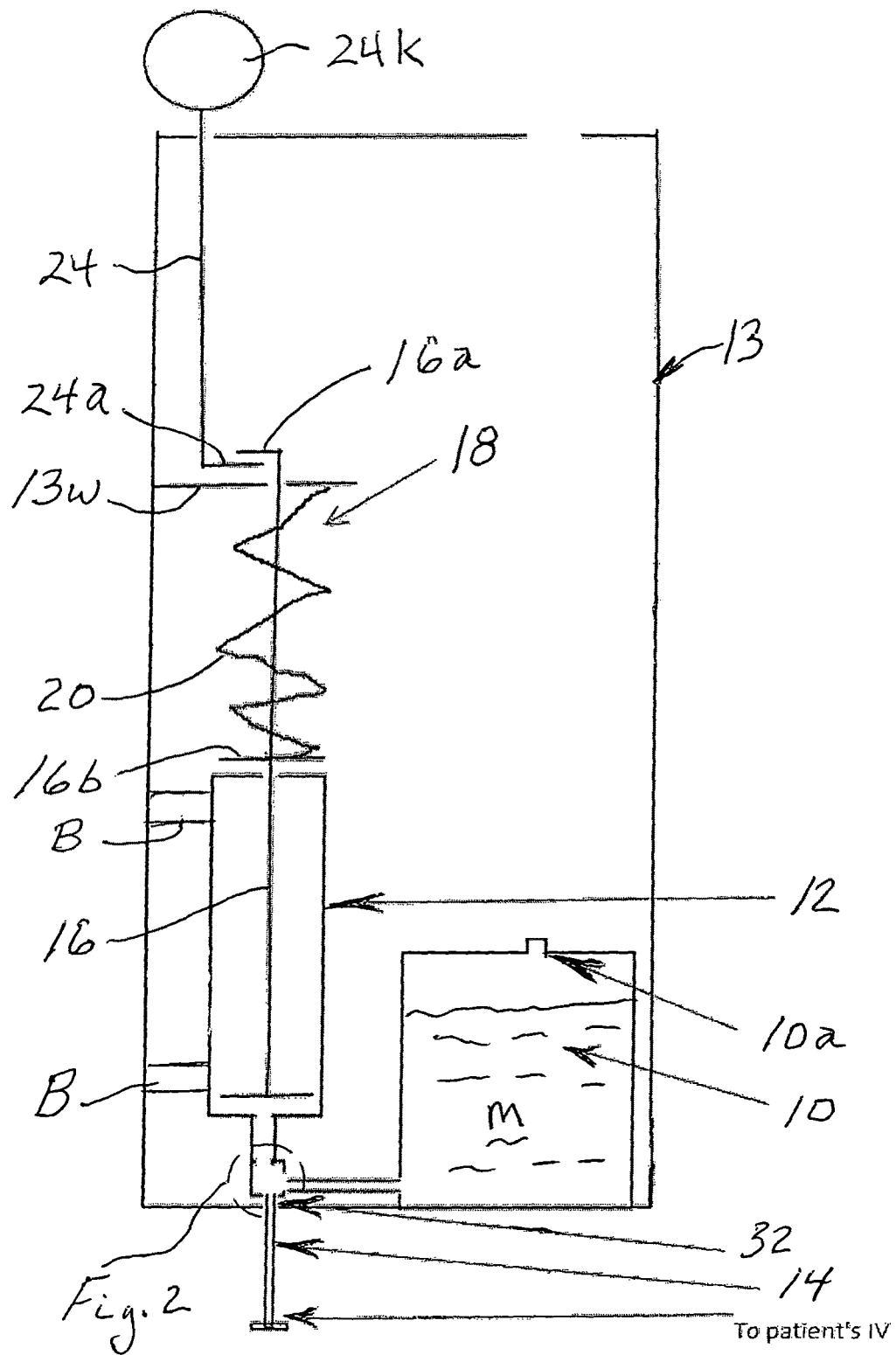
Figure 2:
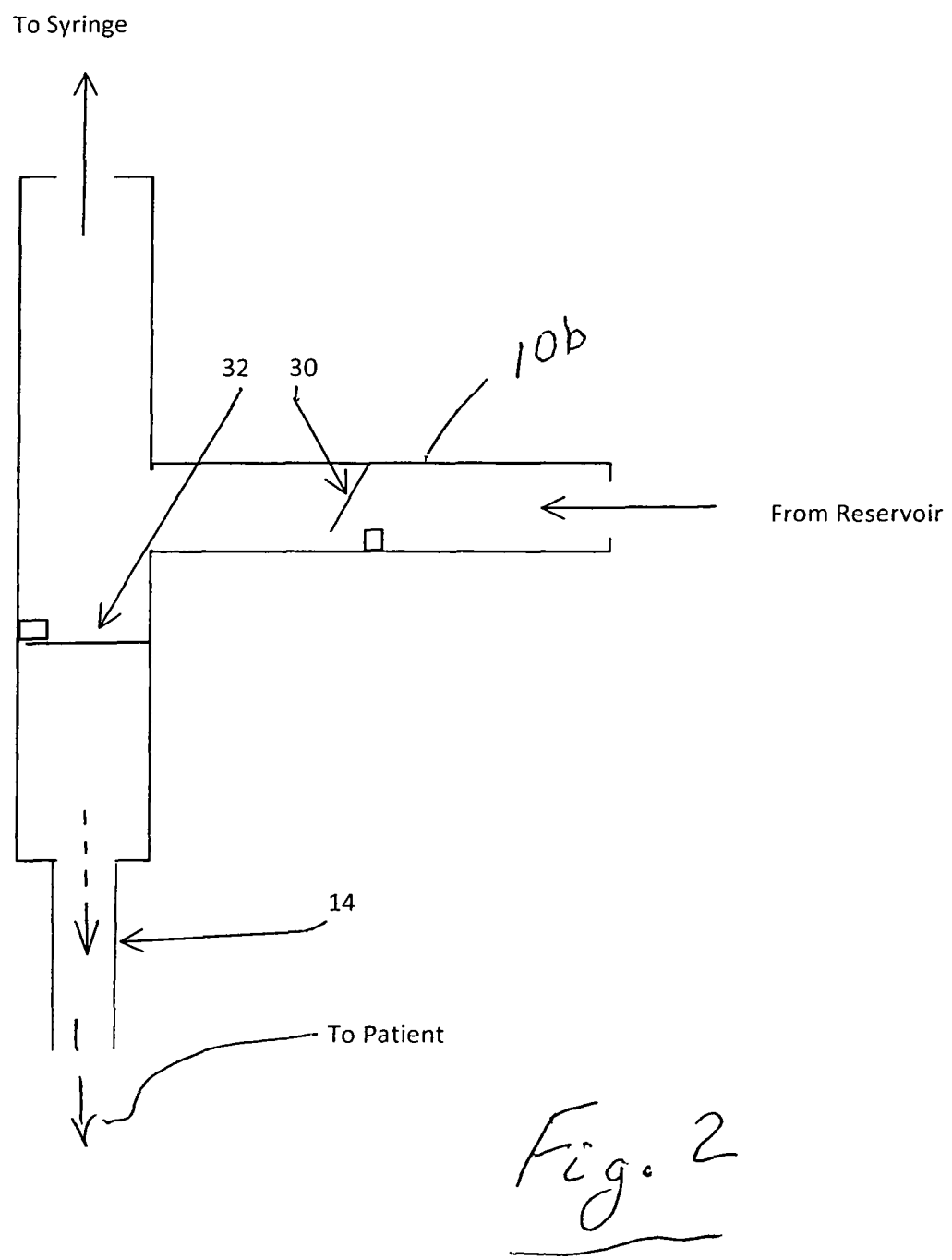
FIG. 2 is an enlarged schematic view of the IV medication reservoir metering element and one-way valves when fluid/medication is being drawn from the reservoir into the syringe (valve from reservoir is open and valve to patient is closed).

FIGS. 1A, 1B and 2 schematically depict an embodiment of the mechanical infusion pump offered for purposes of illustration and not limitation as comprising a medication reservoir 10, such as, for example, a conventional IV medication bag, and a syringe 12 communicated to the IV bag 10 by the valves in FIG. 2. The IV bag 10 is disposed in the container 13 and shown supported on the container bottom for purposes of illustration and not limitation. The syringe 12 is disposed in the container 13 and is fixedly supported by brackets B or other support in container 13. The container 13 includes an opening 13a that allows ambient air to flow into and out of container 13 and a closeable door (not shown).

The IV reservoir 10 is filled via injection port 10a with medication or is preloaded with medication. The container door can be latched shut after a preloaded bag is in position or after medication is added to the IV bag in the container. For purposes of illustration and not limitation, the IV reservoir 10 can be a commercially available IV bag.

The IV medication reservoir 10 includes or is connected to a one-way valve element 30, which is open when fluid medication is being drawn from the IV reservoir 10 into the syringe 12 and is closed when medication is discharged under pressure to the patient's IV as described below.

The syringe 12 includes syringe plunger 16 which is movable upwardly in FIG. 1A in a first syringe-filling direction to draw fluid medication from the IV reservoir 10 into the syringe. The syringe plunger is moved upwardly by a manually operable filling plunger 24 that is movable independently of the syringe plunger 16 and is engaged with but unconnected to the syringe plunger 16 when the filling plunger is moved in the first direction to fill the syringe.

The filling plunger 24 is located above the syringe plunger 16 and includes a flange 24a that engages flange 16a of the syringe plunger 16 when the filling plunger 24 is pulled upwardly by an individual, such as a patient, nurse, doctor, etc. using the plunger knob 24k shown. The releasable engagement between the upper flange 16a and lower flange 24a prevents pressing of the filling plunger 24 by the individual (e.g. patient) from injecting the medication into the patient's intravenous line. For purposes of illustration and not limitation, the syringe 12 with plunger 16 can be a commercially available syringe modified to include a second flange 16b that is spaced from inner wall shoulder 13w of the container 13 wherein the second flange 16b can be integral or connected to the syringe plunger 16.

When the syringe is filled with medication by pulling of the filling plunger 24 as described above, the syringe plunger 16 is biased by a biasing element 18 that is compressed by virtue of being disposed between the syringe plunger flange 16b and fixed container wall 13w and exerts a bias on the syringe plunger 16 in the second (downward) syringe-discharging direction to dispense a calibrated amount of fluid medication to the patient's IV over a unit of time when the filling plunger 24 is released whereby the filling plunger 24 drops downwardly by gravity or under the influence of the biasing element.

For purposes of illustration, the biasing element 18 is shown comprising a compression coil spring 20, which resides around the shaft of the syringe plunger 16 and between the inner-projecting fixed wall 13w of the container 13 and the flange 16b of the syringe plunger 16 as depicted in FIG. 1A such that upward pulling of the filling plunger 24 and thus the syringe plunger 16 in the first direction compresses the biasing element. The fixed wall 13w is integral to or fixedly connected to the container 13. The coil spring is shown fully compressed in FIG. 1A and extended in FIG. 1B. The biasing element 18 is not limited to a compression spring and can comprise an elastic or resilient plastic or rubber sleeve, or other biasing element that can exert a downward bias on the syringe plunger 16 in FIG. 1A, 1B. The top wall 12w of the syringe includes an opening to allow up/down movement of the syringe plunger 16.

Figure 3:
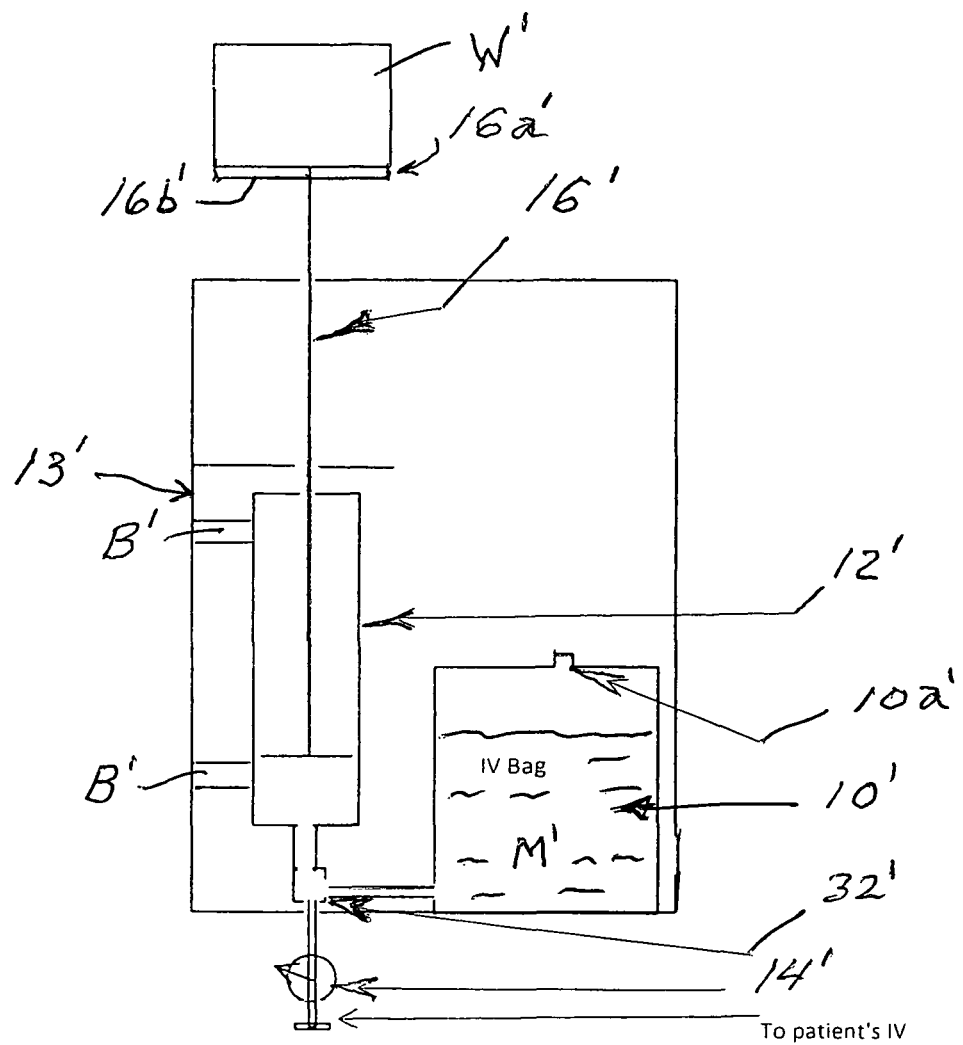
FIG. 3 schematically shows another different embodiment of a mechanical infusion pump device according to the present invention wherein the syringe plunger includes a biasing weight-receiving feature on which one or more biasing weights are received for moving the syringe plunger in the second syringe-discharging direction when the filling plunger is released.

FIG. 3 schematically shows another illustrative embodiment of a mechanical infusion pump device according to the present invention wherein the filling plunger includes a weight-receiving feature on which one or more weights are received for biasing the filling plunger in the second syringe-discharging direction.

In practice of a method embodiment of the present invention, the IV medication reservoir 10 is filled via injection port 10a with fluid medication and injection fluid as needed (collectively designated M in FIG. 1A), the IV bag being connected to syringe 12 via tube 10b and one-way valve 30. The door of box or container 13 is closed and locked.

The syringe 12 is filled by the syringe plunger 16 being moved upwardly in FIG. 1A by manual upward pulling of the filling plunger 24 by the individual patient or caregiver until the syringe is filled with the fluid medication.

The filling plunger 24 then is released such that the syringe plunger 16 is moved by the biasing element 18 extending as shown in FIG. 1B to discharge medication to the patient's IV. The medication cannot be discharged to the patient's IV more rapidly than the biasing element 18 (spring 20) and restricting needle or capillary tube metering element 14 allow for a given fluid viscosity of the medication. The patient's inadvertent pressing on the filling plunger 24 will not cause injection of the medication as explained above due to the flanges 24a and 16a becoming disengaged.

The biasing element 18 (e.g. compression spring 20) and metering element 14 (e.g. capillary tube) are calibrated to allow a specific amount of medication to flow out of the syringe 12 per unit time (e.g., 6 ml in 60 minutes), corresponding to a maximum amount of medication ordered per unit time. Different metering elements and biasing elements can be designed to give different volumes of fluid over time with each injection with the metering element and the biasing element being calibrated for each desired application to this end.

Thus, the mechanical properties of the illustrated device (e.g. spring properties and capillary tube radius for a given fluid viscosity) limit the dose per time interval. In particular, the difference between the height of the spring biasing element 20 when fully compressed and the height of the spring biasing element 20 when fully extended for a given capillary metering tube radius determines the maximum amount of medication discharged from the syringe 12, and hence the maximum dose injected at one time. A different spring/metering element (restrictor) combination can be selected and used in order to adjust the particular volume of fluid/medication for each injection. The biasing element 18 (e.g. spring 20) and metering element (restrictor) 14 are calibrated for each combination. A set of calibrated tubes or valves 14 can be provided and connected so that the tubes or valves 14 can be operational in sequence to allow the operator to increase the dose as needed.

Since the viscosity of water soluble medications approximates that of water, a single biasing element and metering element (restrictor) combination can be used for multiple medications.

Moreover, in an alternate embodiment of the invention when only small quantities of medication are needed, the syringe 12 can be preloaded with the desired quantity of medication that is discharged into the patient's IV line using the biasing element 18 without the need for use of the filling plunger 24, IV medication reservoir 10, and the one-way valve 30 associated with the IV medication reservoir 10. In practicing this method, a quantity of medication is preloaded into the syringe 12 in the usual way by pulling the syringe plunger 16 to an extended position out of the syringe to this end. The preloaded syringe is placed in the container 13 so as to be held in fixed position therein by brackets B with the biasing element 18 compressed. The brackets B can be of a type that are openable/closeable to this end. When the syringe plunger 16 is released, the biasing element 18 biases the syringe plunger 16 in the downward syringe-discharging direction of the filled syringe 12 to dispense a controlled amount of medication into the patient's IV over a unit of time as controlled by the biasing element 18 and the metering element 14, which are calibrated to this end as described above.

FIG. 3 schematically shows a different embodiment of a mechanical infusion pump device according to the present invention wherein that differs from the above embodiments in that the syringe injection plunger 16' includes a biasing weight-receiving feature 16a' on which one or more biasing weights are received for moving by gravity the syringe plunger in the second syringe-discharging direction when the plunger is released after filling the syringe with medication.

For purposes of illustration and not limitation, the biasing weight-receiving feature 16a' can comprise an integral or attached platform 16b' disposed on the upper end of the syringe plunger, FIG. 3, on which platform one or more weights W' are received (one weight shown). The platform 16b' can be molded or fused on the syringe plunger 16', or the platform 16b' can be separate and mechanically attached to the syringe plunger 16' by any joining means. For example, the platform 16b' can include projecting-legs (or other male features) to be received in female features on the syringe plunger.

The biasing weights can be stacked on the platform 16b' of the syringe plunger 16' or releasably fastened using mechanical fasteners of any kind such as using threaded fasteners, clips, and the like and can comprise one or more calibrated weights of any shape to be received on the filling plunger. Plastic encased metal biasing weights can be used, although practice of the invention is not so limited. Calibrated weights are available in many hospital or other care facilities and can be placed on the syringe plunger 16' as described above, or calibrated weights can be provided with the infusion pump device as a kit for use in hospital or care facilities that may not have such weights.

The one or more biasing weights W' and the metering element 14' (e.g. capillary tube or adjustable valve) are calibrated to allow a specific amount of medication to flow out of the syringe 12' per unit time (e.g., 6 ml in 60 minutes), corresponding to a maximum amount of medication ordered per unit time. Different metering elements and weights can be designed to give different volumes of fluid over time with each injection with the metering element and the biasing element being calibrated for each desired application to this end. Thus, the mechanical properties of the illustrated device (e.g. the weights and the metering element for a given fluid viscosity) limit the dose per time interval. The metering element 14' can be adjustable, rather a fixed capillary tube orifice. A set of calibrated weights W' or valves 14' can be used or provided for use on the filling plunger.

Other than the syringe plunger 16' being present sans the filling plunger and carrying the biasing weights W', other features of the infusion pump device of FIG. 3 are similar to those described are given the same reference numerals primed.

For example, in practice of a method embodiment of the present invention relating to FIG. 3, the IV medication reservoir 10' is filled via injection port 10a' with fluid medication and injection fluid as needed (collectively designated M' in FIG. 3), the IV bag being connected to syringe 12' via tube 10b' and one-way valve 30'. The door of box or container 13' is closed and locked.

The syringe 12' is filled by the syringe plunger 16' being moved upwardly in FIG. 3 by manual upward pulling by the individual patient or caregiver until the syringe is filled with the fluid medication.

The syringe plunger 16' then is released so that the downward force of gravity exerted by the one or more weights W' on the syringe plunger 16' moves the syringe plunger 16' in the second syringe-discharging direction to discharge medication to the patient's IV. The medication cannot be discharged to the patient's IV more rapidly than the biasing weight(s) W' and restricting needle or capillary tube or adjustable metering element 14' allow for a given fluid viscosity of the medication.

Figure 4:
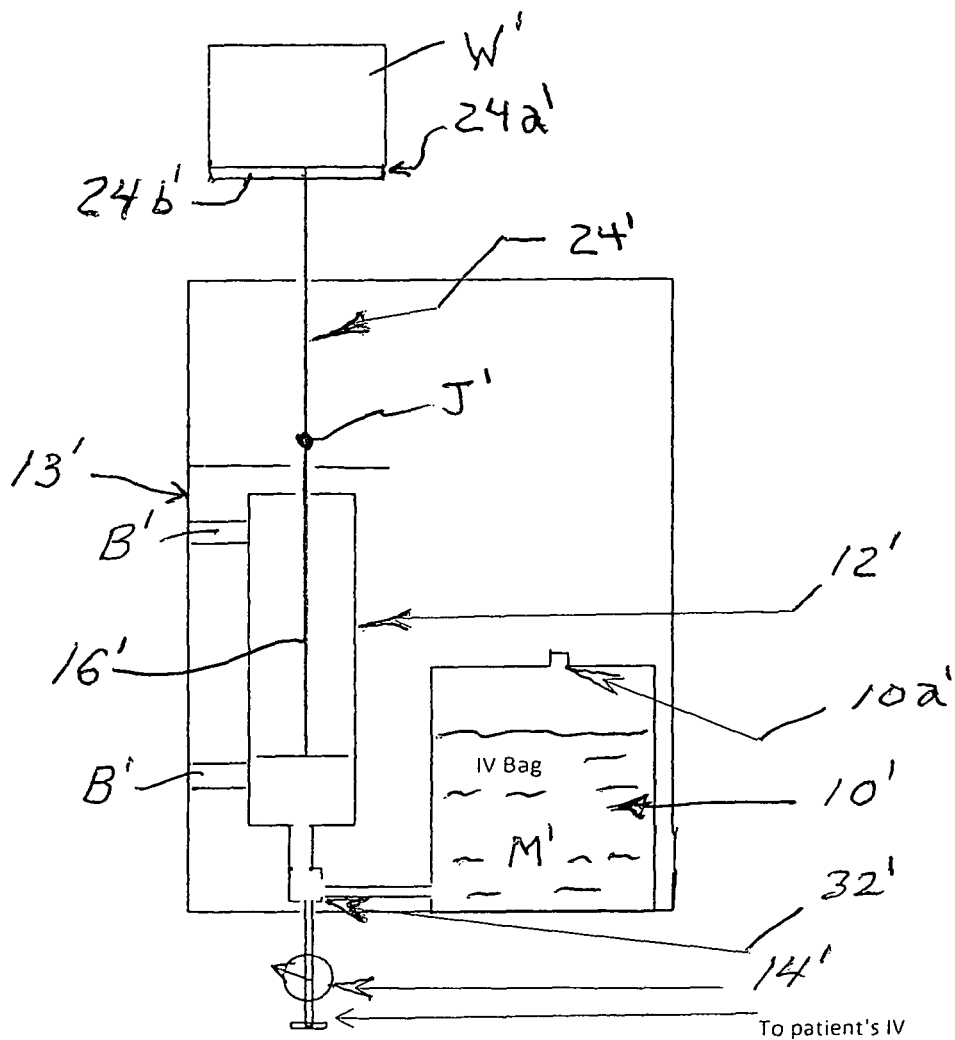
FIG. 4 schematically shows another different embodiment of a mechanical infusion pump device according to the present invention wherein the filling plunger and the syringe plunger are connected for movement together and wherein the filling plunger includes a biasing weight-receiving feature on which one or more biasing weights are received for moving the filling plunger and the syringe plunger in the second syringe-discharging direction when the filling plunger is released.

FIG. 4 schematically shows a different embodiment of a mechanical infusion pump device according to the present invention wherein that differs from the above embodiments in that the filling plunger 24' and the syringe plunger 16' are connected and the filling plunger 24' includes a biasing weight-receiving feature 24a' on which one or more biasing weights are received for moving by gravity the filling plunger and the syringe plunger in the second syringe-discharging direction when the filling plunger is released after filling the syringe with medication.

The filling plunger 24' and the syringe plunger 16' typically connected at a joint J', which can comprise any type of mechanical connection (e.g. using fasteners, clips, and the like) or fused connection (e.g. a fused or glued joint to providing a one-piece filling plunger/syringe plunger) such that the filling plunger and the syringe plunger move together.

The biasing weight-receiving feature 24a' can comprise a integral or attached platform 24b' disposed on the upper end of the filling plunger, FIG. 3, on which platform one or more weights W' are received (one weight shown), although the weight-receiving feature can comprise an annular shoulder on the filling plunger to receive one or more annular weights, one or more hooks on the filling plunger to receive one or more weights, or any other surface on the filling plunger that can receive one or more biasing weights W'. The biasing weights can be held on the filling plunger 24' using mechanical fasteners of any kind such as using clips, hooks and the like and can comprise one or more calibrated weights of any shape to be received on the filling plunger. Plastic encased metal biasing weights can be used, although practice of the invention is not so limited. Calibrated weights are available in many hospital or other care facilities and can be placed on the filling plunger 24' as described above, or calibrated weights can be provided with the infusion pump device as a kit for use in hospital or care facilities that may not have such weights.

The one or more biasing weights W' and the metering element 14' (e.g. capillary tube or adjustable valve) are calibrated to allow a specific amount of medication to flow out of the syringe 12' per unit time (e.g., 6 ml in 60 minutes), corresponding to a maximum amount of medication ordered per unit time. Different metering elements and weights can be designed to give different volumes of fluid over time with each injection with the metering element and the biasing element being calibrated for each desired application to this end. Thus, the mechanical properties of the illustrated device (e.g. the weights and the metering element for a given fluid viscosity) limit the dose per time interval. The metering element 14' can be adjustable, rather a fixed capillary tube orifice. A set of calibrated weights W' or valves 14' can be used or provided for use on the filling plunger.

Other than the filling plunger 24' and syringe plunger 16' being connected and the weights W' being received on the filling plunger, other features of the infusion pump device of FIG. 3 are similar to those described are given the same reference numerals primed.

For example, in practice of a method embodiment of the present invention relating to FIG. 3, the IV medication reservoir 10' is filled via injection port 10a' with fluid medication and injection fluid as needed (collectively designated M in FIG. 3), the IV bag being connected to syringe 12' via tube 10b' and one-way valve 30'. The door of box or container 13' is closed and locked.

The syringe 12' is filled by the syringe plunger 16' being moved upwardly in FIG. 3 by manual upward pulling of the connected filling plunger 24' by the individual patient or caregiver until the syringe is filled with the fluid medication.

The filling plunger 24' then is released so that the downward force of gravity exerted by the one or more weights W' on the filling plunger 24' force the filling plunger 24' and the syringe plunger 16' to move iin the second syringe-discharging direction to discharge medication to the patient's IV. The medication cannot be discharged to the patient's IV more rapidly than the biasing weight(s) W' and restricting needle or capillary tube or adjustable metering element 14' allow for a given fluid viscosity of the medication.

The infusion pump device described above may be fabricated of conventional medical parts (syringe, restricting needle, connecting tubing, valves and IV medication bag), but using components specifically designed for the device could make it simpler and easier to set up. The device thus can be very low cost and hence disposable. The above-described embodiments of the device do not comprise any electrical or electro-mechanical parts, although such parts may be incorporated into the device. For example, the biasing element 18 may be replaced by an electrical or electromechanical (solenoid) biasing element.

The device has potential uses in pre-hospital (ambulance) care, acute/urgent care clinics, birthing clinics, emergency departments, intensive care units and other sites where infusions of medications are needed.

It is noted that, as used in this specification and the appended claims, the singular forms "a," "an," and "the," include plural referents unless expressly and unequivocally limited to one referent. As used herein, the term "include" and its grammatical variants are intended to be non-limiting, such that recitation of items in a list is not to the exclusion of other like items that can be substituted or other items that can be added to the listed items.

Upon studying the disclosure, it will be apparent to those skilled in the art that various modifications and variations can be made in the devices and methods of various embodiments of the invention within the scope of the appended claims. Other embodiments will be apparent to those skilled in the art from consideration of the specification and practice of the embodiments disclosed herein. It is intended that the specification and examples be considered as examples only.

I claim:

1. An infusion device, comprising an IV medication reservoir, a syringe communicated to the IV medication reservoir and having a syringe plunger operable by an individual to move the syringe plunger in a first syringe-filling direction, said syringe plunger having a biasing weight-receiving feature on which one or more biasing weights are disposed to move the syringe plunger in a second syringe-discharging direction when the syringe is filled and the syringe plunger is released to dispense an amount of medication per unit of time to a patient's IV.

2. The device of claim 1 wherein the biasing weight-receiving feature comprises a surface on the syringe plunger on which one or more of the biasing weights can be placed.

3. The device of claim 2 wherein the surface is a platform on the syringe plunger.

4. The device of claim 1 including said one or more biasing weights and a fixed or adjustable metering element between the syringe and the patient's IV to provide a specific amount of medication to flow out of the syringe per unit time.

5. The device of claim 1 further including a one-way valve to prevent medication from being transferred from the syringe back into the IV medication reservoir when the syringe plunger is moved in the second direction.

6. The device of claim 1 further including a second one-way valve to prevent flow of medication from the patient's IV back to the syringe when the syringe plunger is moved in the first direction.

7. The device of claim 1 wherein the syringe plunger includes a manually operable outer end used to move the syringe plunger in the first syringe-filling direction.

8. The device of claim 1 further including a container in which the IV medication reservoir, the syringe, and the syringe plunger are enclosed.

9. A method of injecting medication into a patient's IV, comprising placing one or more biasing weights on a syringe plunger or a filling plunger that is connected to a syringe plunger, drawing medication from an IV medication reservoir into a syringe by moving the syringe plunger in a first syringe-filling direction, and moving the syringe plunger in a second syringe-discharging direction by the force of the one or more weights after the syringe is filled to dispense a controlled amount of medication into the patient's IV over a unit of time.

10. The method of claim 9 including calibrating said one or more biasing weights and a metering element located between the syringe and the patient's IV to provide a specific amount of medication to flow out of the syringe per unit time.

* * * * *